(12) United States Patent
Sloman

(10) Patent No.: US 6,714,819 B1
(45) Date of Patent: Mar. 30, 2004

(54) SYSTEM AND METHOD OF AUTOMATICALLY ADJUSTING AUTO CAPTURE SAFETY MARGIN

(75) Inventor: Laurence S. Sloman, West Hollywood, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/524,462

(22) Filed: Mar. 13, 2000

(51) Int. Cl.⁷ .................................................. A61N 1/18
(52) U.S. Cl. ....................................................... 607/28
(58) Field of Search ................................. 607/28, 27, 9

(56) References Cited

U.S. PATENT DOCUMENTS

| | | | |
|---|---|---|---|
| 4,686,988 A | 8/1987 | Sholder | 128/419 |
| 4,708,142 A | 11/1987 | DeCote, Jr. | 128/419 |
| 4,712,555 A | 12/1987 | Thornander et al. | 128/419 |
| 4,729,376 A | 3/1988 | DeCote, Jr. | 128/419 |
| 4,788,980 A | 12/1988 | Mann et al. | 128/419 |
| 4,809,697 A | 3/1989 | Causey, III et al. | 128/419 |
| 4,940,052 A | 7/1990 | Mann et al. | 128/419 |
| 4,944,298 A | 7/1990 | Sholder | 128/419 |
| 4,944,299 A | 7/1990 | Silvian | 128/419 |
| 4,955,376 A | 9/1990 | Callaghan et al. | 128/419 |
| 4,969,462 A | 11/1990 | Callaghan et al. | 128/419 |
| 4,969,467 A | 11/1990 | Callaghan et al. | 128/419 |
| 5,350,410 A | 9/1994 | Kleks et al. | 607/28 |
| 5,466,254 A | 11/1995 | Helland | 607/123 |
| 5,573,550 A | 11/1996 | Zadeh et al. | 607/28 |
| 5,601,615 A | 2/1997 | Markowitz et al. | 607/28 |
| 5,683,431 A | 11/1997 | Wang | 607/28 |
| 5,685,315 A | 11/1997 | McClure et al. | 128/708 |
| 5,713,933 A | 2/1998 | Condie et al. | 607/28 |
| 5,766,229 A | 6/1998 | Bornzin | 607/28 |
| 5,855,594 A | 1/1999 | Olive et al. | 607/28 |
| 5,861,012 A | 1/1999 | Stroebel | 607/28 |

Primary Examiner—Mark Bockelman

(57) ABSTRACT

An implantable stimulation device delivers a stimulation pulse in a chamber of a patient's heart and perform periodic threshold tests for generating a statistical model of the threshold data, to minimize the number of threshold tests required over a given time. Based on this statistical model, the stimulation pulse energy is automatically adjusted to a level that minimizes the risk of loss of capture. The auto-capture safety margin is determined by the variability of the threshold data accumulated over time such that a minimum safety margin can be set to ensure that the delivered pulse energy always exceeds the threshold level. The timing of the trigger events is continuously adjusted to be proportional to the variability of the threshold data. If the standard deviation of the threshold measurements increases, the trigger would occur more often. If the standard deviation decreases, the trigger would be adjusted automatically to occur less often. In this way, when the threshold is less stable, more frequent threshold tests will result in more frequent adjustments to the stimulation pulse energy in accordance with the patient's need. When the threshold is stable, less frequent threshold tests are performed and fewer adjustments to the stimulation pulse energy are needed.

13 Claims, 7 Drawing Sheets

SYSTEM AND METHOD OF AUTOMATICALLY ADJUSTING AUTO CAPTURE SAFETY MARGIN

FIELD OF THE INVENTION

The present invention relates in general to cardiac stimulation devices, such as pacemakers, defibrillators, cardioverters, implantable cardioverter-defibrillators ("ICDs"), and similar cardiac stimulation devices that are capable of monitoring and detecting electrical activities and events within the heart. In particular, this invention pertains to a system and method for automatically adjusting the energy of the stimulation pulse so as to automatically set the threshold safety margin based on a series of threshold tests for optimal energy expenditure.

BACKGROUND OF THE INVENTION

Implantable pacemakers generate electrical stimulation pulses and deliver such stimulation pulses to atrial and/or ventricular muscle tissue of a patient's heart at a prescribed rate and/or rhythm when, through disease or other causes, the heart is not able to maintain the prescribed heart rate or rhythm on its own. When the delivered electrical stimuli are of sufficient energy, they cause the cardiac muscle tissue to depolarize, and therefore contract, thereby forcing the heart rate or rhythm to track the delivery of the electrical stimuli. When the delivered electrical stimuli are of insufficient energy, depolarization does not occur, and the heart rate or rhythm is not controlled by the pacemaker. Hence, for the pacemaker to perform its intended function, it is critically important that the delivered electrical stimuli be of sufficient energy to depolarize the cardiac tissue, a condition known as "capture".

The energy of the electrical stimuli generated by an implanted pacemaker is derived from the energy stored in the pacemaker power source or battery. The pacemaker battery has a limited amount of energy stored therein, and the generation of electrical stimuli represents by far the greatest drain of such energy. In order to preserve this limited energy and to prolong the life of the battery, it is known in the art to adjust the energy of the delivered electrical stimuli so that it is just sufficient to cause capture, with an appropriate safety margin.

Capture detection may occur on a beat-by-beat basis or on a sampled basis. In one embodiment, a capture threshold search is performed once a day during at least the acute phase (e.g. the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold. For a more detailed description of capture and the implementation of capture detection circuitry and algorithms refer, for example, to U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al); and U.S. Pat. No. 5,350,410 (Kleks et. al), all of which patents are hereby incorporated herein by reference.

The amount of energy needed to effectuate capture is known as the capture "threshold", and electrical stimuli of energy less than the capture threshold do not bring about capture, while electrical stimuli of energy greater than the capture threshold do bring about capture. By adjusting the energy of the electrical stimuli so that it is always greater than the capture threshold, but not too much greater, the limited energy of the pacemaker battery may thus be preserved. The battery energy is preserved because: (1) electrical stimuli of insufficient energy to cause capture (electrical stimuli below threshold), which stimuli represent wasted energy, are rarely generated; and (2) electrical stimuli of excessive energy (energy much greater than the capture threshold), which excess energy not only represents wasted energy, but also energy that may disadvantageously cause pectoral stimulation and/or sensation, are also rarely generated.

In general, capture verification has been regarded as a process that must be carried out continually, and conventional methods teach that capture must be verified with each and every stimulus so that a servomechanism within the pacemaker can provide a backup pulse in the event that a first pulse fails to provide capture and so that the energy of the next stimulation pulse can be adjusted upward. Reference is made to U.S. Pat. Nos. 4,969,467; 4,969,462; and 4,955,376.

However, capture verification requires a significant amount of processing time and corresponding battery current to be expended. An important aspect of conventional capture verification is setting the safety margin (also referred to as safety factor) is normally set to a fixed value. The safety margin value is determined largely by limitations in the hardware platforms that allow programmed amplitude steps of, for example, 0.125 Volt.

In ventricular auto capture systems, the safety margin has proven to be adequate since beat-by-beat capture verification is provided by the pacemaker. If a threshold increase occurs, the pacemaker responds by increasing the output amplitude, and re-finding the capture threshold, where the safety margin is applied. This method reduces the energy consumption by adding the lowest possible safety margin the pacemaker allows. Reference is made to U.S. Pat. No. 5,766,229 to Bornzin, which is incorporated herein by reference.

However, beat by beat capture verification may not be provided in atrial automatic threshold determination, resulting in a need for higher safety margins. Also, threshold variability has been demonstrated to be greater sometimes due for example to circadian variations, sinus rate variability and other factors that are present in the atrium but not necessarily in the ventricle. The problem that remains heretofore unresolved is to choose the safety margin that guarantees capture and at the same time provides adequate energy savings in an atrial and ventricular automatic threshold testing device.

In addition, conventional pulse energy is set based on the result of a single threshold test and a certain fixed safety margin. As a result, threshold testing must be repeated often to adjust the safety margin. This conventional approach may result in "under-sampling", which can lead to erroneous conclusions and an unstable pacing system. Under-sampling the threshold in turn requires frequent threshold tests, causing additional inefficiencies of the pacing system.

In view of the above, it is evident that there is still an unsatisfied need for an automatic threshold testing method that automatically adjusts the atrial and ventricular threshold safety margins and that minimizes the expenditure of battery current.

SUMMARY OF THE INVENTION

The present invention addresses the above and other needs by providing an implantable pacemaker wherein an automatic threshold testing is performed to generate a statistical model. The statistical analysis of a series of threshold tests is then used to adjust the safety margin based on statistically determined threshold and safety margin such that the possibility of a loss of capture episode is minimized.

The threshold testing in accordance with the present invention occurs when a defined trigger event initiates a testing algorithm. Such testing, because it is performed on a limited sampled basis, advantageously limits the time and power needed by the electronic circuitry (typically a microprocessor) to perform the tests, thereby conserving power and freeing up the circuitry for other processes.

Thus, in accordance with one aspect of the invention, the expenditure of battery current in the pacemaker is minimized because threshold tests are performed only on a limited sampled basis, and not with every capture verification test as is traditionally practiced in the art. Periodic threshold tests can therefore be performed less often.

A further aspect of the invention provides for adjustment of the pulse energy based on the statistical analysis of a minimal sample size of threshold tests. A pulse energy based on such a statistical analysis will provide greater confidence that the stimulation pulse energy is equal to or greater than the threshold, thereby minimizing the possibility of a loss of capture event. It is thus seen that the present invention reduces the required frequency of capture verification since greater confidence of capture exists.

In addition, the present invention addresses the problem of potential risk of non-capture by setting the stimulating pulse energy to a value that improves the confidence that capture will occur with every stimulation pulse, thus justifying the use of less frequent capture verification.

The present invention addresses the problem of under-sampling that results from the determination of the pulse energy based on a single threshold test, that requires frequent or over-sampling of capture verification by determining the pulse energy from a series of threshold tests over time, and by setting the threshold and safety margin to levels that minimize the chance that capture will be lost.

The threshold testing algorithm of the present invention includes: setting a specified number of threshold tests that will occur over a specified period of time; performing the threshold tests at the specified points in time and storing the threshold test result; calculating descriptive statistical data for the stored threshold test result; and adjusting the stimulating pulse energy based on the variability of the threshold test results.

It is still a further feature of the invention to provide an implantable pacemaker wherein once the desired number of threshold tests have been performed the stimulation pulse energy is set to value that is the lowest possible value, based on the statistical analysis of the threshold tests, that predicts, with a desired degree of confidence, that capture will occur with every stimulation pulse.

BRIEF DESCRIPTION OF THE DRAWINGS

The above and further features, advantages and benefits of the present invention will be apparent upon consideration of the present description taken in conjunction with the accompanying drawings, in which.

DETAILED DESCRIPTION OF THE PREFERRED EMBODIMENTS

The following description is of a best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
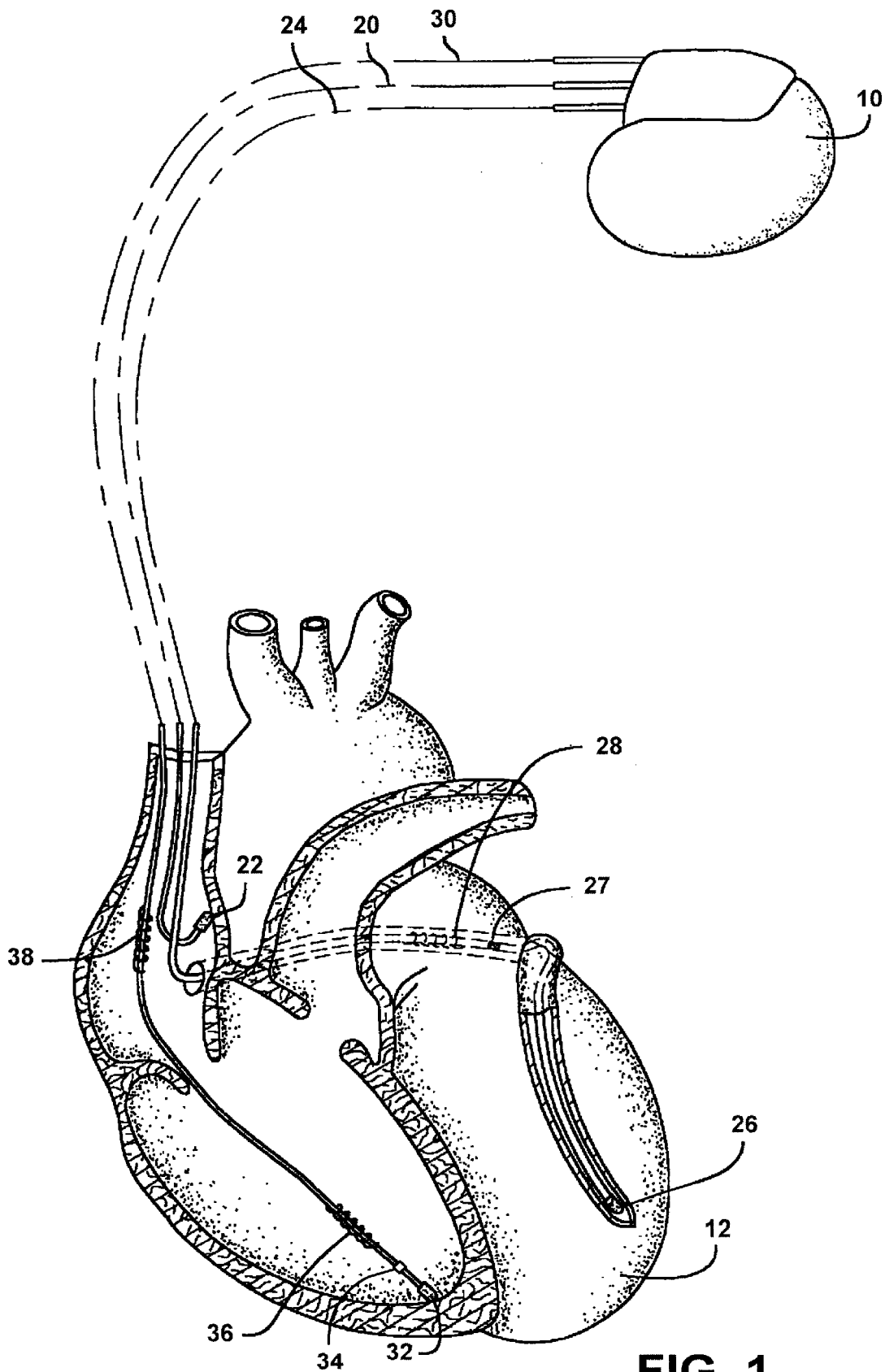
FIG. 1 is a simplified, partly cutaway view illustrating an implantable stimulation device in electrical communication with at least three leads implanted into a patient's heart for delivering multi-chamber stimulation and shock therapy.

FIG. 1 illustrates a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left-chamber pacing therapy, the stimulation device 10 is coupled to a "coronary sinus" lead 24 designed for placement in the "coronary sinus region" via the coronary sinus os so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver: left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, refer to U.S. patent application Ser. No. 09/457,277, filed Dec. 8, 1998, titled "A Self-Anchoring, Steerable Coronary Sinus Lead" (Pianca et. al); and U.S. Pat. No. 5,466,254, titled "Coronary Sinus Lead with Atrial Sensing Capability" (Helland), which patent application and patent are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
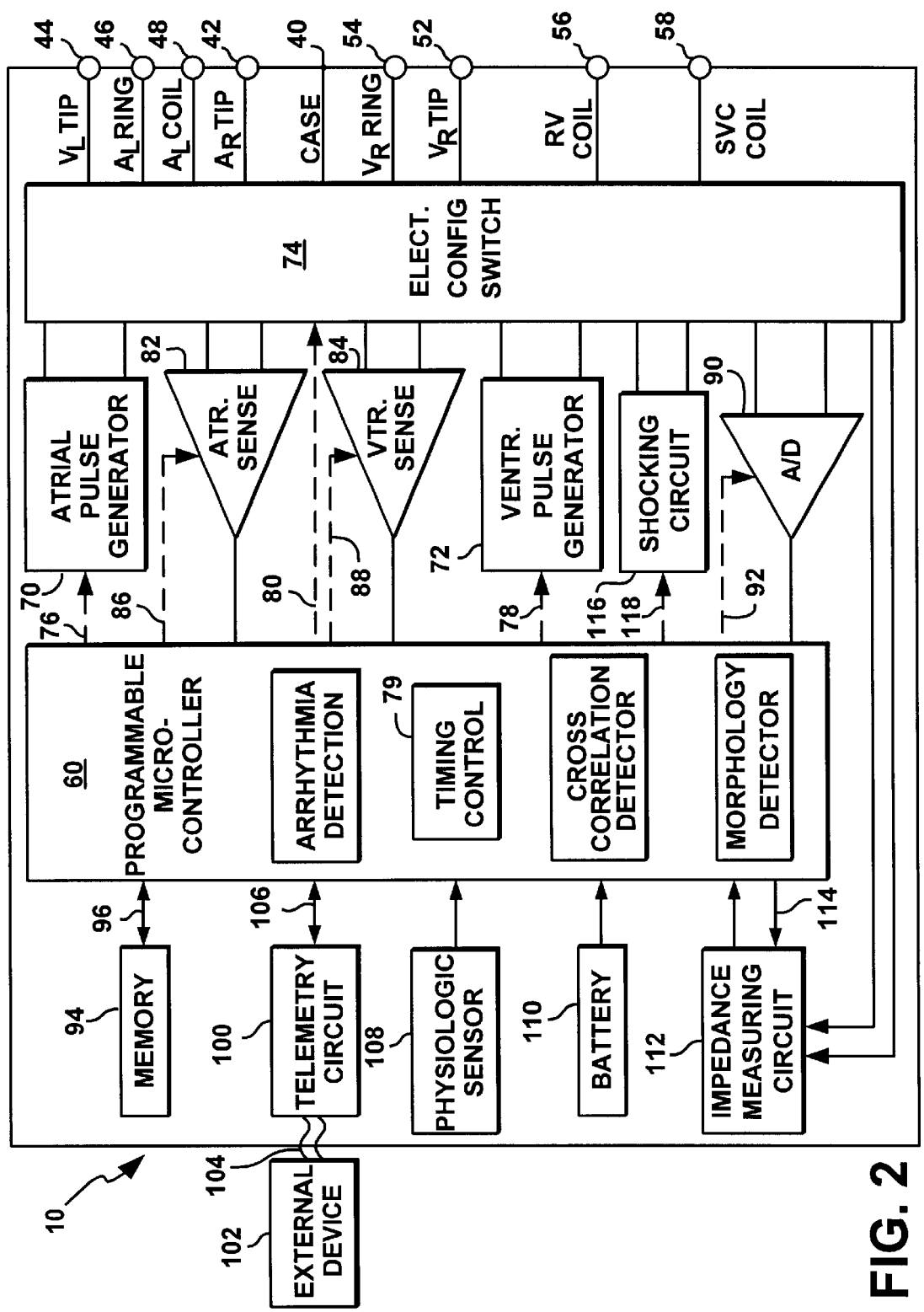
FIG. 2 is a functional block diagram of the multi-chamber implantable stimulation device of FIG. 1, illustrating the basic elements that provide cardioversion, defibrillation and/or pacing stimulation in four chambers of the heart.

FIG. 2 illustrates a simplified block diagram of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and/or pacing stimulation.

The stimulation device 10 includes a housing 40 which is often referred to as "can", "case" or "case electrode", and which may be programmably selected to act as the return electrode for all "unipolar" modes. The housing 40 may further be used as a return electrode alone or in combination with one or more of the coil electrodes 28, 36, or 38, for shocking purposes. The housing 40 further includes a connector (not shown) having a plurality of terminals, 42, 44, 46, 48, 52, 54, 56 and 58 (shown schematically and, for convenience, the names of the electrodes to which they are connected are shown next to the terminals). As such, to achieve right atrial sensing and pacing, the connector includes at least a right atrial tip terminal 42 adapted for connection to the atrial ($A_R$) tip electrode 22.

To achieve left chamber sensing, pacing and/or shocking, the connector includes at least a left ventricular ($V_L$) tip terminal 44, a left atrial ($A_L$) ring terminal 46, and a left atrial ($A_L$) shocking terminal (coil) 48, which are adapted for connection to the left ventricular tip electrode 26, the left atrial tip electrode 27, and the left atrial coil electrode 28, respectively.

To support right chamber sensing, pacing and/or shocking, the connector further includes a right ventricular ($V_R$) tip terminal 52, a right ventricular ($V_R$) ring terminal 54, a right ventricular (RV) shocking terminal (coil) 56, and an SVC shocking terminal (coil) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. As is well known in the art, the microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

Representative types of control circuitry that may be used with the present invention include the microprocessor-based control system of U.S. Pat. No. 4,940,052 (Mann et. al), and the state-machine of U.S. Pat. No. 4,712,555 (Sholder) and U.S. Pat. No. 4,944,298 (Sholder). For a more detailed description of the various timing intervals used within the stimulation device and their inter-relationship, refer to U.S. Pat. No. 4,788,980 (Mann et. al). The '052, '555; '298; and '980 patents are incorporated herein by reference.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via a switch bank 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g. pacing rate, atrio-ventricular (AV) delay, atrial interconduction (A-A) delay, or ventricular interconduction (V-V) delay, etc.), as well as to keep track of the timing of refractory periods, PVARP intervals, noise detection windows, evoked response windows, alert intervals, marker channel timing, etc.

The switch bank 74 includes a plurality of switches for connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g. unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch bank 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch bank 74 determines the "sensing polarity" of the cardiac signal by selectively closing the appropriate switches. In this way, the clinician may program the sensing polarity independent of the stimulation polarity.

Each of the atrial sensing circuit 82 or the ventricular sensing circuit 84 preferably employs one or more low power, precision amplifiers with programmable gain and/or automatic gain control, bandpass filtering, and a threshold detection circuit, to selectively sense the cardiac signal of interest. The automatic gain control enables the stimulation device 10 to deal effectively with the difficult problem of sensing the low amplitude signal characteristics of atrial or ventricular fibrillation.

For a more complete description of a typical sensing circuit, refer to U.S. Pat. No. 5,573,550, titled "Implantable Stimulation Device having a Low Noise, Low Power, Precision Amplifier for Amplifying Cardiac Signals" (Zadeh et. al). For a more complete description of an automatic gain control system, refer to U.S. Pat. No. 5,685,315, titled "Cardiac Arrhythmia Detection System for an Implantable Stimulation Device" (McClure et. al). The '550 and '315 patents are hereby incorporated herein by reference.

The outputs of the atrial and ventricular sensing circuits 82 and 84 are connected to the microcontroller 60 for triggering or inhibiting the atrial and ventricular pulse generators 70 and 72, respectively, in a demand fashion, in response to the absence or presence of cardiac activity, respectively, in the appropriate chambers of the heart. The atrial and ventricular sensing circuits 82 and 84, in turn, receive control signals over signal lines 86 and 88 from the microcontroller 60, for controlling the gain, threshold, polarization charge removal circuitry (not shown), and the timing of any blocking circuitry (not shown) coupled to the inputs of the atrial and ventricular sensing circuits 82 and 84.

For arrhythmia detection, the stimulation device 10 utilizes the atrial and ventricular sensing circuits 82 and 84 to sense cardiac signals, for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g. P-waves, R-waves, and depolarization signals associated with fibrillation which are sometimes referred to as "F-waves" or "Fib-waves") are then classified by the microcontroller 60 by comparing them to a predefined rate zone limit (e.g. bradycardia, normal, low rate VT, high rate VT, and fibrillation rate zones) and various other characteristics (e.g. sudden onset, stability, physiologic sensors, and morphology, etc.) in order to determine the type of remedial therapy that is needed (e.g. bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes.

Advantageously, the data acquisition system 90 may be coupled to the microcontroller 60 or another detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing circuitry within the microcontroller 60, and enabling the data acquisition system 90 via control signal 92 to sample the cardiac signal that falls in the capture detection window and, based on the amplitude of the sampled cardiac signal, determines if capture has occurred.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. A feature of the stimulation device 10 is the ability to sense and store a relatively large amount of data (e.g. from the data acquisition system 90), which data may then be used for subsequent analysis to guide the programming of the stimulation device 10.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through the established communication link 104. For examples of such devices, refer to U.S. Pat. No. 4,809,697, titled "Interactive Programming and Diagnostic System for use with Implantable Pacemaker", (Causey, III et al.); U.S. Pat. No. 4,944,299, titled "High Speed Digital Telemetry System for Implantable Device" (Silvian); and U.S. patent application Ser. No. 09/223,422, filed Dec. 30, 1998, titled "Efficient Generation of Sensing Signals in an Implantable Medical Device such as a Pacemaker or ICD" (McClure et al.), all of which are hereby incorporated herein by reference.

In a preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g. detecting sleep and wake states). Accordingly, the microcontroller 60 responds by adjusting the various pacing parameters (such as rate, AV Delay, V-V Delay, etc.) at which the atrial and ventricular pulse generators 70 and 72 generate stimulation pulses.

While the physiologic sensor 108 is shown as being included within the stimulation device 10, it is to be understood that the physiologic sensor 108 may alternatively be external to the stimulation device 10, yet still be implanted within, or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors which sense the oxygen content of blood, respiration rate and/or minute ventilation, pH of blood, ventricular gradient, etc. However, any sensor may be used which is capable of sensing a physiological parameter which corresponds to the exercise state of the patient.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time, and also be capable of providing high-current pulses (for capacitor charging) when the patient requires a shock pulse. The battery 110 must preferably have a predictable discharge characteristic so that elective replacement time can be detected. Accordingly, the stimulation device 10 can employ lithium/silver vanadium oxide batteries.

The stimulation device 10 further includes a magnet detection circuitry (not shown), coupled to the microcontroller 60. The purpose of the magnet detection circuitry is to detect when a magnet is placed over the stimulation device 10, which magnet may be used by a clinician to perform various test functions of the stimulation device 10 and/or to signal the microcontroller 60 that an external programmer 102 is in place to receive or transmit data to the microcontroller 60 through the telemetry circuit 100.

As further shown in FIG. 2, the stimulation device 10 is shown as having an impedance measuring circuit 112 which is enabled by the microcontroller 60 by a control signal 114. Certain applications for an impedance measuring circuit 112 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of the valves, etc. The impedance measuring circuit 112 is advantageously coupled to the switch bank 74 so that any desired electrode may be used.

It is a primary function of the stimulation device 10 to operate as an implantable cardioverter/defibrillator (ICD) device. That is, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high (11 to 40 Joules) energy, as controlled by the microcontroller 60. Such shocking pulses are applied to the patient's heart through at least two shocking electrodes, and as shown in this embodiment, selected from the left atrial coil electrode 28, the RV coil electrode 36, and/or the SVC coil electrode 38 (FIG. 1). As noted above, the housing 40 may act as an active electrode in combination with the RV electrode 36, or as part of a split electrical vector using the SVC coil electrode 38 or the left atrial coil electrode 28 (i.e., using the RV electrode as common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asychronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
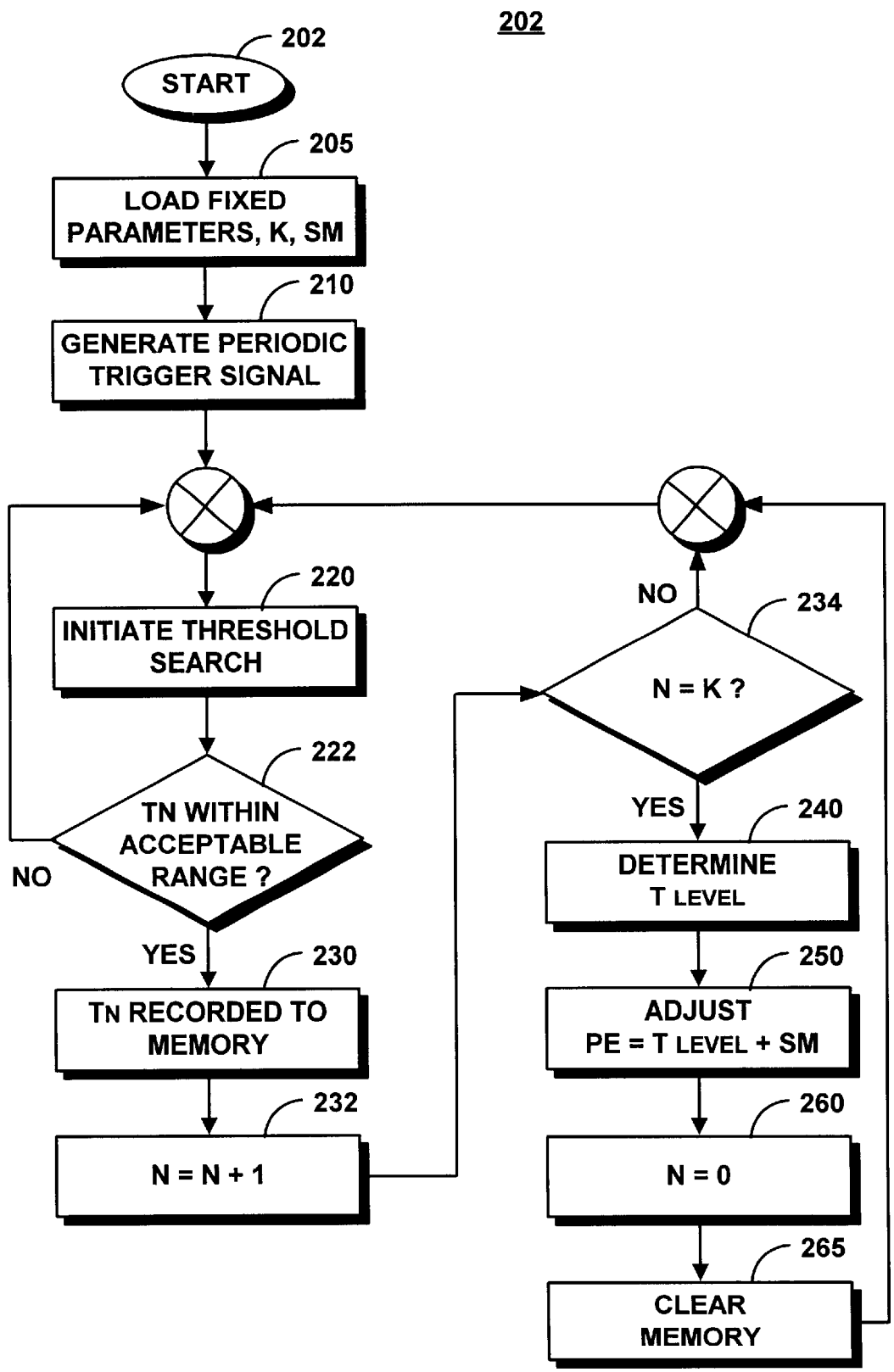
FIG. 3 is a flow chart illustrating an overview of the operation and features implemented in one embodiment of the stimulation device of FIGS. 1 and 2.

In FIG. 3, a flow chart is shown describing an overview of the operation and features implemented in one embodiment of the stimulation device 10. In this flow chart, and the other flow charts described herein, the various algorithmic steps are summarized in individual "blocks". Such blocks describe specific actions or decisions that must be made or carried out as the algorithm proceeds. Where the microcontroller 60 (or its equivalent) is employed, the flow charts presented herein provide the basis for a "control program" that may be executed or used by such a microcontroller 60 (or its equivalent) to effectuate the desired control of the stimulation device.

In this embodiment, the control program is comprised of multiple integrated program modules, with each module bearing responsibility for controlling one or more functions of the stimulation device 10. For example, one program module may control the delivery of stimulating pulses to the heart 12, while another may control the verification of ventricular capture and ventricular pacing energy determination. In effect, each program module is a control program dedicated to a specific function or set of functions of the stimulation device 10.

In particular, a program module is implemented by the stimulation device 10 to perform periodic threshold tests for generating a statistical model of the threshold, T, and to thereby minimize the number of threshold tests required over a given time. Based on this statistical model of the threshold T, the stimulation pulse energy, PE, is automatically adjusted to a level that minimizes the risk of loss of capture. Furthermore, the safety margin, SM, is determined by the variability of the threshold data accumulated over time such that a minimum safety margin can be set to ensure that the delivered pulse energy always exceeds the threshold to a specified degree of confidence. While two exemplary program modules 200 and 300 are depicted in the flow charts of FIGS. 3 and 7, respectively, it should be understood that alternative program modules can be used.

With reference to FIG. 3, the program module 200 starts at step 202, and uploads fixed parameters, such as a sampling number K, from the memory 94 at step 205. At step 210, the timing control circuitry 79 (FIG. 2) of the control system 30 generates a periodic trigger signal to initiate the threshold test. The timing of the periodic trigger can be programmed in the memory 94 by the practitioner. The interval between two consecutive trigger events or signals could be expressed either in units of time or cardiac cycles.

Figure 8:
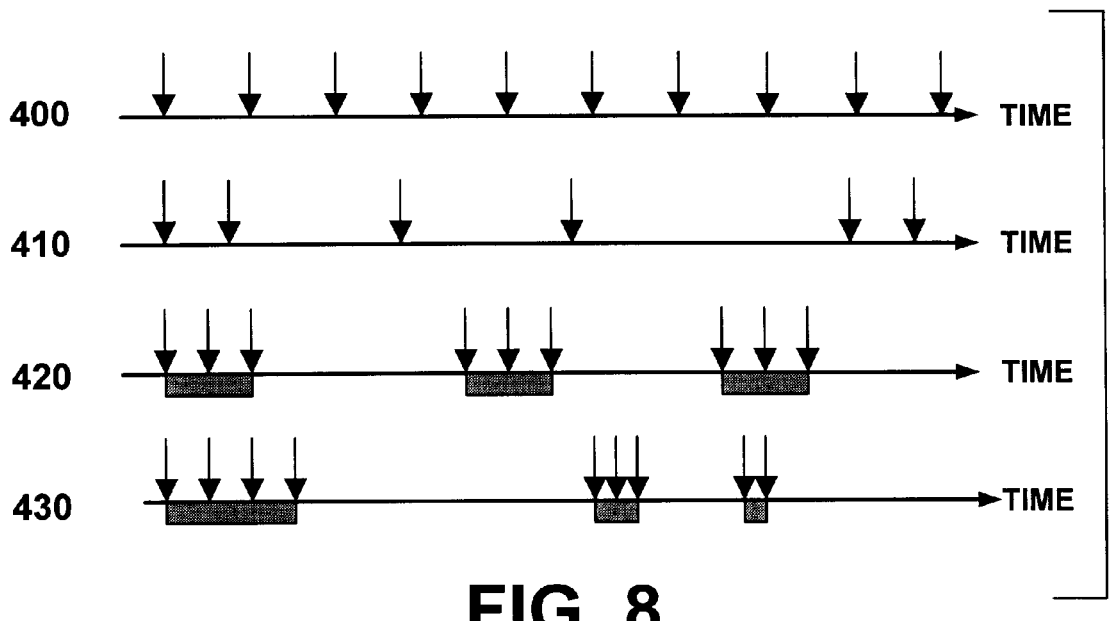
FIG. 8 is an illustration that depicts various modes of triggering the operation of the stimulation device.

As shown in FIG. 8, various modes could be used in determining the periodicity of the trigger events. Based on the incorporation of a real-time clock in the timing control circuitry 79 (FIG. 2), the trigger events can be programmed to occur at a fixed interval of time, as illustrated by the downward pointing arrows on the time line 400. Alternatively, the trigger events can be programmed to occur at a random interval, as illustrated by the downward pointing arrows on the time line 410.

The trigger events could also occur at constant intervals within a specified period of time to be repeated after a defined delay, as illustrated by the downward pointing arrows on the time line 420. For example, a trigger event could be initiated every ten minutes during a thirty-minute period every twelve hours, resulting in six threshold tests per day. Still another variation is a trigger event occurring at random intervals within a specified period of time to be repeated after a defined delay, as illustrated by the downward pointing arrows on the time line 430. Several variations or combinations of such trigger event timing modes are possible, and the modes illustrated in FIG. 8 are meant to be exemplary, not exclusive.

According to a preferred embodiment, the timing of the trigger event is continuously adjusted by the control system 30 to be proportional to the variability of the threshold. If the standard deviation, $\sigma$, of N threshold measurements increases, the trigger would occur more often. If, and when the standard deviation decreases, the trigger would be adjusted automatically to occur less often. In this way, when the threshold is less stable, more frequent threshold tests will result in more frequent adjustments to the stimulation pulse energy PE in accordance with the patient's need. When the threshold is stable, less frequent threshold tests are performed and fewer adjustments to the stimulation pulse energy are needed.

Once a trigger event occurs at step 210, a threshold search algorithm is initiated at step 220. Any appropriate algorithm for determining threshold can be employed. One such method is taught in U.S. Pat. No. 5,766,229 to Bornzin, in which, after a specified period of stable cardiac rhythm, a high level stimulation pulse is delivered at a shorter interval than the stable rhythm and progressively decremented until loss of capture is detected. Threshold is then defined as the last stimulation pulse energy at which capture was verified. Other algorithms are possible such as starting with a stimulation pulse energy equal to the most recently determined threshold and verifying capture. If capture is verified, the stimulation pulse energy is reduced until capture is lost. If capture is not verified, then the stimulation pulse energy is increased until capture is detected.

During the threshold search test, capture will be detected as generally taught in the art. An evoked response in the atria following an atrial test pulse is received at the atrial sense amplifier 82 (FIG. 2). Likewise, an evoked response in the ventricles following a ventricular test pulse is received at the ventricular sense amplifier 84 (FIG. 1). An output signal from either the atrial sense amplifier 82 or ventricular sense amplifier 84, is received by the microcontroller 60 where it is interpreted as a capture event. Other physiological signals, such the mechanical contraction of the heart muscle or the pulse pressure waveform can also be used for verifying capture.

After the threshold search is completed, the resulting threshold value, $T_N$, is compared to an acceptable range of values, at step 222, to verify that the result is valid. If the threshold value $T_N$ is not acceptable, a threshold search will be performed again. If $T_N$ is acceptable, it will be recorded in the memory 94 at step 230.

Figure 6:
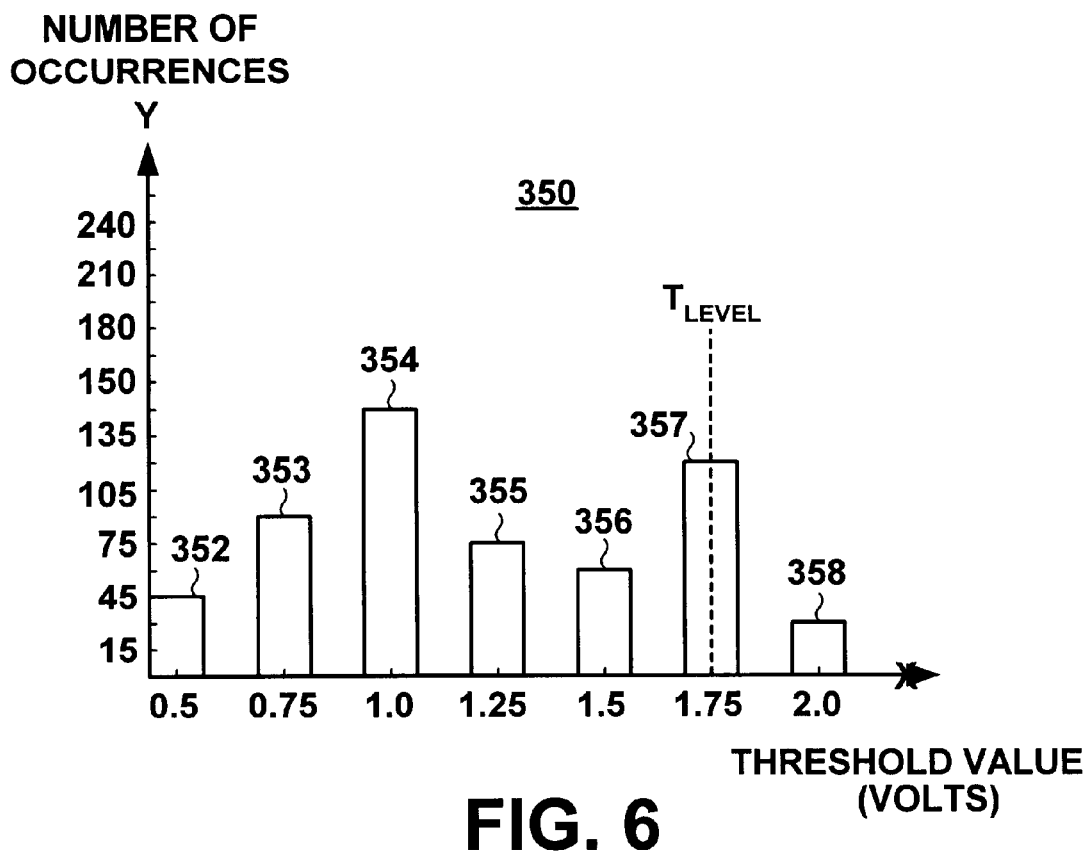
FIG. 6 is an exemplary histogram that illustrates the process of selecting a threshold level according to the present invention.

This will result in incrementing the number stored in one particular bin in a histogram 350 of FIG. 6. For example, the particular threshold value $T_N$ is stored in bin 352. The program module generates a collection of data such as that depicted as the histogram 350. Each bin or histogram column, e.g. 352, 353, 354, 355, 356, 357, 358, represents a stimulation pulse energy (PE) setting available to the stimulation device 10. The height, or Y-value, of each histogram column represents the number of threshold tests resulting in a threshold value equal to the stimulation pulse energy assigned to a particular bin.

A memory counter or bin is assigned to each stimulating pulse energy setting available in the stimulation device 10. The counter or bin assigned to the stimulation pulse energy is incremented by one at step 232 for incrementing the threshold test.

Returning to FIG. 3, each time a threshold test result $T_N$ is recorded in the memory 94, a sample number counter, N, is incremented by one at step 232, and compared to a desired sample number, K, at step 234. In a preferred embodiment, the desired sample number is a user-programmable variable. If the sample number N is less than the desired sample number K, the program module returns to wait for the next trigger event at 210, and repeats steps 220, 222, 230, 232 and 234, as described above. If, however, at step 234, the program module determines that adequate samples N have been collected, a determination of the descriptive statistics of the threshold data will be performed at step 240. The results will be used to adjust the stimulation pulse energy at step 250, as will be described below.

The program module determines the desired threshold level ($T_{LEVEL}$) by selecting a particular threshold bin of the histogram 350 (FIG. 6). According to one embodiment, the threshold level is set equal to the threshold value (along the X-axis) assigned to the uppermost bin. In the example of FIG. 6, the selected threshold value is 1.0 Volt, which corresponds to bin 354. According to another embodiment, the threshold level is set equal to 1.75 Volts, which corresponds to bin 357. In this latter embodiment, the threshold value would be safer than those for bins 352–356, and would be desirable even though it ignores a minimal number of events in bin 358 that occur at a higher threshold value (e.g. 2 Volts) because the statistical probability of the threshold falling near this value is greatest.

Figure 5:
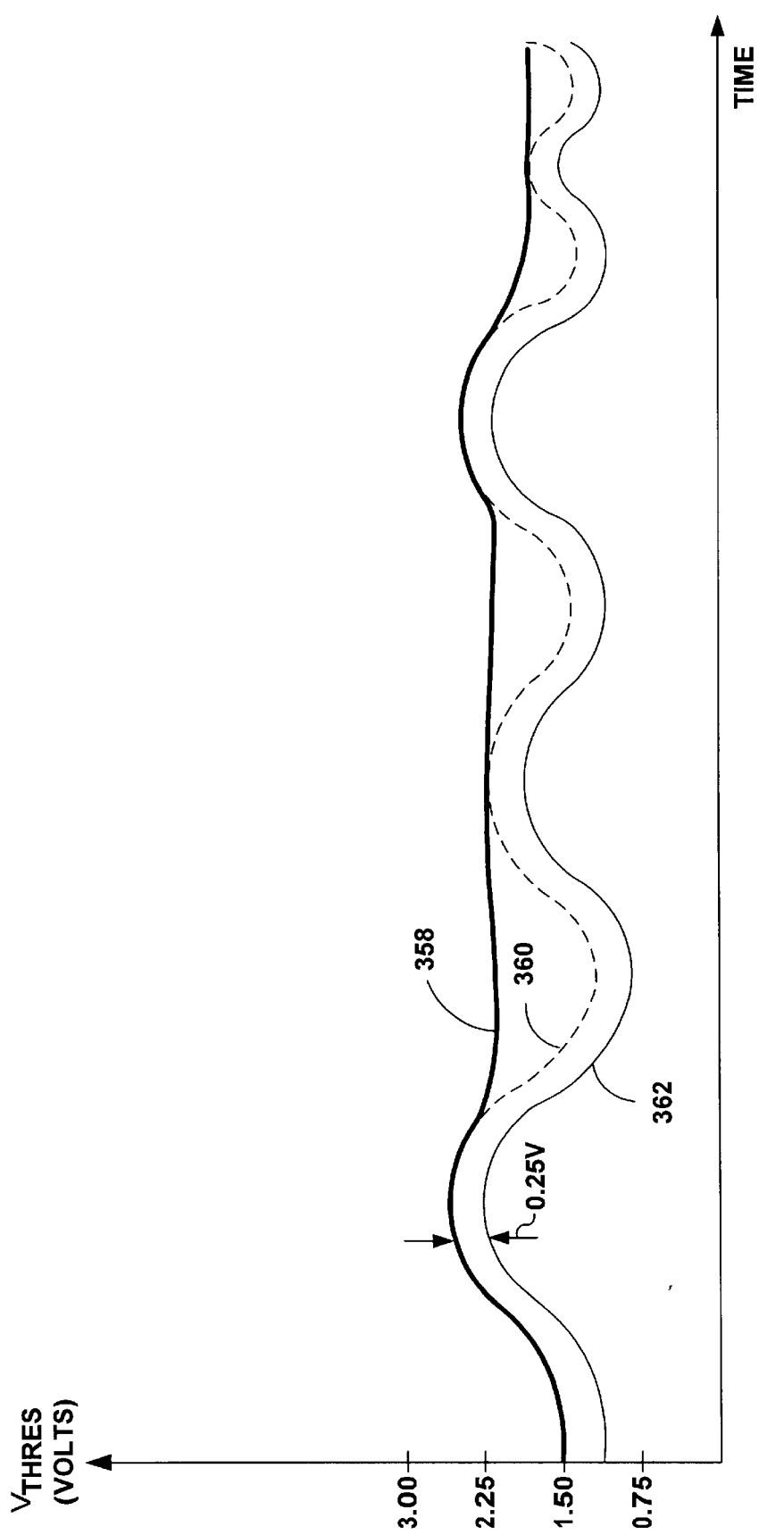
FIG. 5 is a chart that graphically illustrates the operation shown in FIG. 3 over an extended period of time.

It can therefore be appreciated that the stimulation energy pulse curve 358 illustrated in FIG. 5 is a function of the variability of the threshold level in that the stimulation pulse energy level is reduced when the threshold values do not change significantly over time. In other terms, the stimulation pulse energy 358 is a function of the slope (i.e., rate of change) of a threshold or stimulation curve 362.

The program module adjusts the stimulation pulse energy (PE) at step 250 of FIG. 3 by setting the stimulation pulse energy equal to the sum of the selected threshold value $T_{LEVEL}$, and a user programmable safety margin (SM), as expressed by the following equation:

$$PE = T_{LEVEL} + SM.$$

After K threshold searches have been performed and the stimulation pulse energy has been adjusted, the sample number counter N is set to 0 at step 260, and the histogram bins (i.e., 352–358) are cleared from memory at step 265. This will reduce or eliminate anomalous data. The program module loops back and waits for the next trigger event (step 210), and repeats steps 220, 222, 230, 232, 234, 240 and 250, as described above, for new threshold search results to begin to accumulate upon the next series of trigger events.

According to an alternative embodiment, instead of clearing the histogram bins from memory, the memory could be a rolling memory, and the memory capacity would be set such that a fixed number of threshold searches can be recorded. Once this capacity is full, the oldest data point written to memory would be deleted to allow the next new threshold search test to be recorded. In other words, K samples would exist in memory at all times. A rolling memory would prevent a delay in the response time required by the stimulation device to adjust the stimulation pulse energy due to the time required to collect K new samples. Rather than having to acquire K new threshold search results before the stimulation pulse energy can be adjusted can be adjusted after each threshold search. If Tn represents a change in the threshold level, the stimulation pulse energy would be adjusted immediately based on this change Tn, rather than wait for K samples to be collected.

Figure 4:
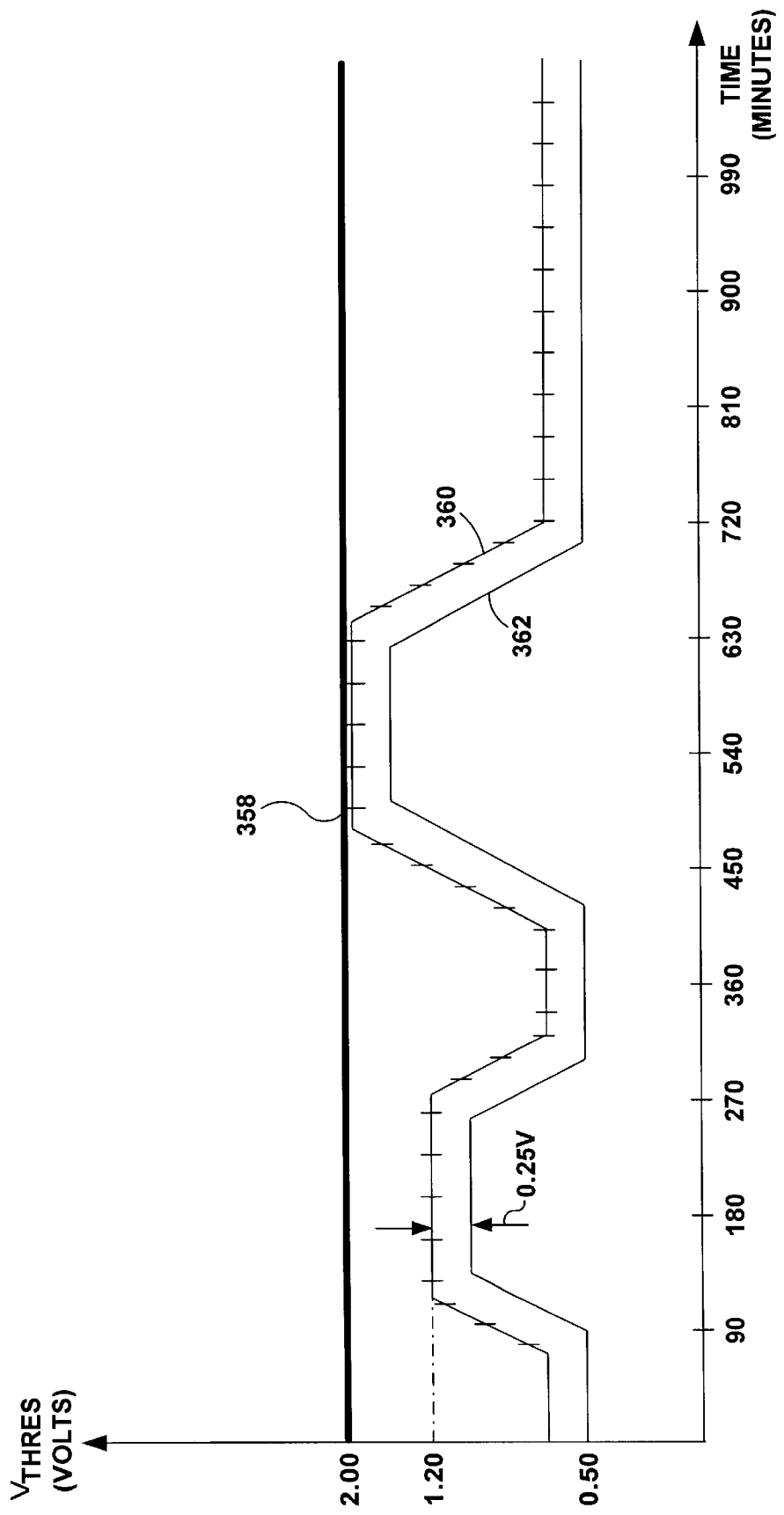
FIG. 4 is a chart that graphically illustrates the operation shown in FIG. 3 over a short period of time.

The operation of the program module of the present invention is further portrayed graphically in FIG. 4, where changes in the threshold value are shown over a relatively short period of time, and the resulting stimulation pulse energy 358 is compared to the stimulation curve 360 which would have been obtained using conventional capture techniques. According to this exemplary stimulation curve 360, the safety margin is set and plotted above a threshold curve 362. At each hash mark, a threshold search is performed, at frequent intervals, or on a beat-by-beat basis, and the stimulation pulse energy is adjusted to the sum of threshold curve 362 and a user-programmed fixed safety margin. In the example of FIG. 4, the safety margin is fixed to 0.25 Volt (it being understood that other values can alternatively be selected).

Since the stimulation pulse energy curve 358 obtained using the present autocapture method remains unchanged (i.e., flat) over an extended period of time, threshold searching would be performed less frequently. This would probably result in a higher stimulation pulse energy than the curve 360, but fewer threshold searches are required, thus reducing the overall battery expenditure and the detrimental hemodynamic effects associated with short AV and PV intervals. Another advantage of the present invention is that stimulation pulse energy is reset based on the results of N threshold tests rather than a single event, thereby providing greater confidence of capture over time.

Figure 7:
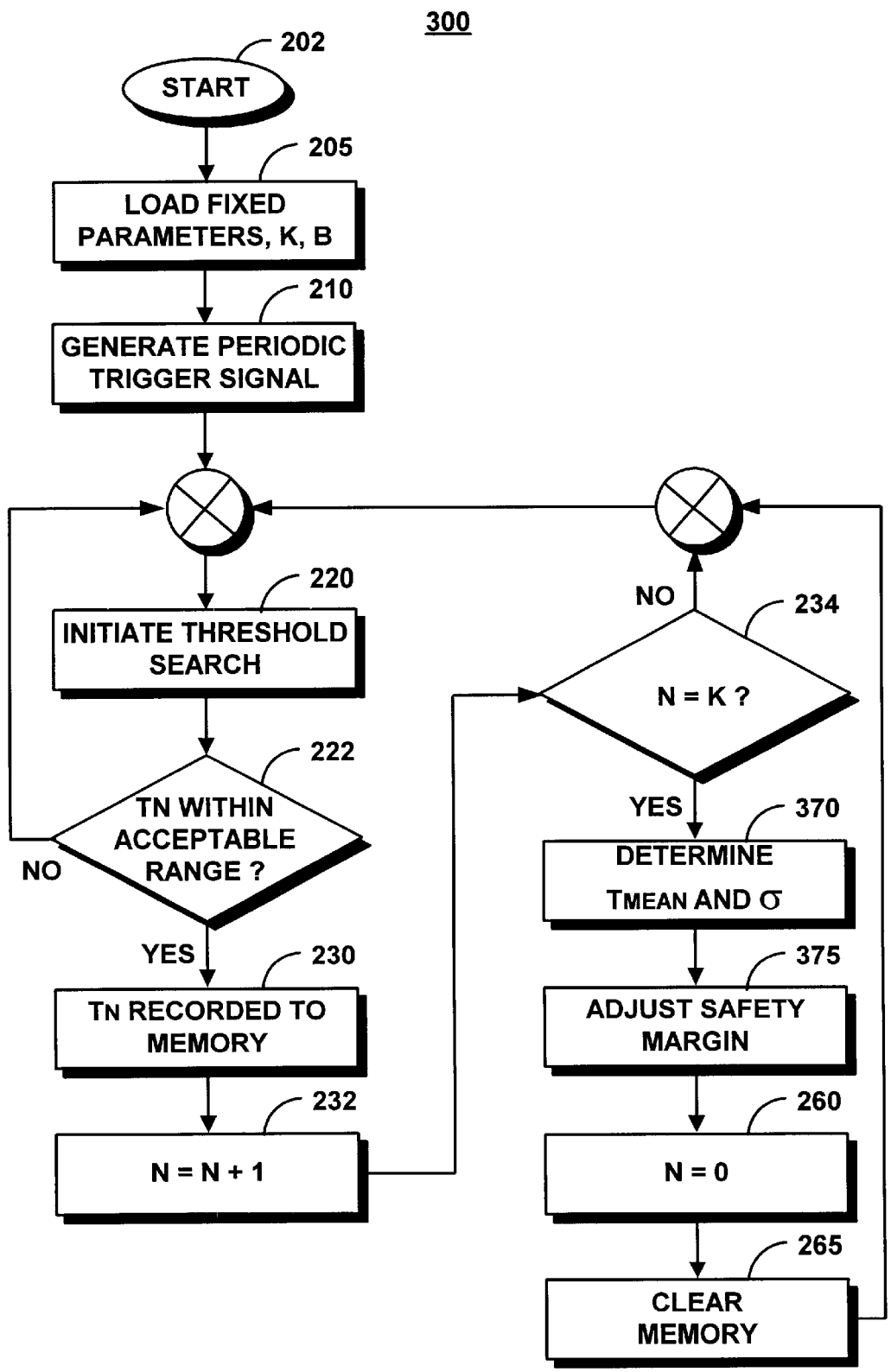
FIG. 7 is a flow diagram that illustrates another mode of operation of the stimulation device of FIGS. 1 and 2.

Another mode of operation of the stimulation device 10 is illustrated in the flow chart of FIG. 7. The steps or blocks that are labeled with similar numeral references as in FIG. 3, indicate the use of the same steps, and thus the description of these steps will not be repeated.

In the alternative embodiment of FIG. 7, upon the completion of K threshold tests, statistical calculations which characterize the threshold level ($T_{LEVEL}$) are performed at step 370. These calculations can include, but are not limited to: the mean threshold ($T_{MEAN}$), the maximum threshold level ($T_{MAX}$), the variability of the threshold ($\sigma^2$), and the standard deviation of the threshold ($\sigma$). Selected statistical data is then used to adjust PE. In the process 300 of FIG. 7, a safety margin (SM) is first calculated based on the standard deviation of the threshold, and is expressed by the following equation:

$$SM = \sigma * B,$$

where B is a user programmed factor.

Next, the stimulation pulse energy is adjusted, and is expressed by the following equation:

$$PE = T_{MEAN} + SM,$$

where $T_{MEAN}$ is calculated by averaging the threshold search results over a predetermined period of time. Assuming a normal distribution of the threshold, the stimulation pulse energy will be adjusted at step 375, to $T_{MEAN}$ plus a user-defined number of standard deviations which will ensure a certain degree of confidence that the stimulation pulse energy is greater than the selected threshold level. The statistical distribution of the threshold determines the minimum safety margin. The confidence interval is determined by the user-programmed factor B.

Other statistical distributions of the threshold may be encountered, and alternative statistical parameters may be used to determine the stimulation pulse energy. The added advantage of this mode of operation is that the stimulation pulse energy is minimized by using the lowest safety margin possible to ensure a desired level of confidence that capture will always occur. This lower stimulation pulse energy will further improve battery longevity.

Since a certain amount of time is required for K threshold search samples to be collected and the statistical model of the threshold generated, it is possible that the response time for the stimulation pulse energy adjustment lags behind a sudden increase in the threshold. One method of overcoming this potential lag is included in the operation of FIG. 7. After the resulting threshold value $T_N$ is recorded to memory at step 222, it is compared to the previous threshold search result, $T_{N-1}$. If $T_N$ is greater than $T_{N-1}$, then a trend of increasing the threshold is indicated. As a safety measure, the stimulation pulse energy PE could be immediately adjusted to a higher temporary value, PE(temp) equal to the higher $T_N$ plus the safety margin. The temporary value PE(temp) would remain as the stimulation energy until the completion of K threshold searches, at which time calculation of new statistical parameters will allow determination of the appropriate stimulation pulse energy.

Numerous variations in the foregoing method can be made without departing from the scope of the present invention, namely, performing threshold searches in order to generate a statistical model of the threshold, reducing the total number of threshold searches by requiring only a desired sample number of searches, and using the statistical results to adjust the stimulation pulse energy. For example, the exact number of threshold searches, the time interval between successive searches, and the user-programmed factor B for calculating the safety margin could be variables based on the stability of the threshold rather than fixed values.

Further, when the stimulation device 10 is rate-responsive, the control parameters that set the trigger events, the sample number, and the factors used in calculating the stimulation pulse energy could also be automatically adjusted as a function of the same physiological parameters that set the pacing rate.

As described above, it is thus seen that the present invention provides a method for performing threshold searches on a sampled basis in order to improve battery longevity by reducing the overall number of threshold tests performed, and to improve patient safety and comfort by determining the stimulation pulse energy based on the statistical characteristics of threshold, thereby predicting, with a desired degree of confidence, that the stimulation pulse energy will always be greater than the threshold.

While the invention herein disclosed has been described by means of specific embodiments and applications thereof, numerous modifications and variations could be made therein by those skilled in the art without departing from the scope of the invention.

What is claimed is:

1. A stimulation device for automatically adjusting a stimulation pulse energy, comprising:
   a pulse generator for generating a stimulation pulse to trigger an evoked response;
   a sense circuit for sensing the evoked response to determine a capture threshold value;
   a control system for performing a threshold test by causing the pulse generator to generate a series of trigger stimulation pulses and the sense circuit to confirm resulting captures, in order to generate a threshold statistical model; and
   a power source, which, based on the threshold statistical model, automatically adjusts the stimulation pulse energy to a level that reduces the risk of loss of capture.

2. The stimulation device as recited in claim 1, wherein the control system sets an autocapture threshold safety margin as a function of a variability of the threshold statistical model over time.

3. The stimulation device as recited in claim 2, wherein the control system sets the autocapture threshold safety margin by adding a predetermined margin to a threshold level determined from the threshold statistical model.

4. The stimulation device as recited in claim 3, wherein the predetermined margin is a fixed value.

5. The stimulation device as recited in claim 4, wherein the predetermined margin is approximately 0.25 Volt.

6. The stimulation device as recited in claim 1, wherein the control system generates a plurality of trigger pulses at constant intervals.

7. The stimulation device as recited in claim 1, wherein the control system generates a plurality of trigger pulses at random intervals.

8. The stimulation device as recited in claim 2, wherein the control system generates a plurality of trigger pulses at intervals that are continuously adjusted to be proportional to the variability of the threshold statistical model.

9. The stimulation device as recited in claim 3, wherein the control system generates a plurality of trigger pulses at intervals that vary with a standard deviation of the threshold level.

10. The stimulation device as recited in claim 1, wherein the threshold statistical model includes a histogram.

11. The stimulation device according to claim 10, wherein the control system selects a threshold level based on the number of captures accumulated in a plurality of bins of the histogram, with each bin corresponding to a stimulating pulse energy setting.

12. The stimulation device according to claim 1, wherein the control system generates a threshold statistical model by calculating a safety margin (SM) based on a standard deviation ($\sigma$) of the threshold value, wherein the safety margin is expressed as follows:

$$SM = \sigma * B,$$

where B is a predefined factor.

13. The stimulation device according to claim 12, wherein the control system calculates a mean threshold value ($T_{MEAN}$) by averaging thresholds values over a predetermined period of time, and sets the stimulation pulse energy (PE) as follows:

$$PE = T_{MEAN} + SM.$$

* * * * *